United States Patent [19]

Labbe et al.

[11] Patent Number: 4,725,555
[45] Date of Patent: Feb. 16, 1988

[54] ZINC PROTOPORPHYRIN TEST SYSTEM

[75] Inventors: Robert F. Labbe; Rebecca L. Rettmer, both of Seattle, Wash.

[73] Assignee: Helena Laboratories Corporation, Beaumont, Tex.

[21] Appl. No.: 921,519

[22] Filed: Oct. 22, 1986

[51] Int. Cl.$^4$ .................. G01N 1/28; G01N 21/64; G01N 33/48

[52] U.S. Cl. .................. 436/74; 250/459.1; 356/36; 436/81; 436/96; 436/98; 436/172; 436/174; 436/176; 436/910

[58] Field of Search .................. 436/63, 66, 74, 81, 436/96, 98, 129, 172, 174, 176, 910, 171; 356/36; 250/459.1, 461.2

[56] References Cited

U.S. PATENT DOCUMENTS

| | | | |
|---|---|---|---|
| 3,663,175 | 5/1972 | Depositar et al. | 436/66 |
| 3,874,852 | 4/1975 | Hamill | 436/63 |
| 3,973,129 | 8/1976 | Blumberg et al. | 422/55 X |
| 4,055,768 | 10/1977 | Bromberg | 250/461.2 |
| 4,178,917 | 12/1979 | Shapiro | 356/39 X |

OTHER PUBLICATIONS

Blumberg et al, Clin. Chem., vol. 23, No. 2, pp. 270-274, 1977.

*Primary Examiner*—Barry S. Richman
*Assistant Examiner*—Robert J. Hill, Jr.
*Attorney, Agent, or Firm*—Cullen, Sloman, Cantor, Grauer, Scott & Rutherford

[57] ABSTRACT

A system for determining zinc protoporphyrin levels in whole blood using hematofluorometry without the need for oxygenation of the hemoglobin by derivatizing the hemoglobin to form a new compound having essentially the same spectral properties as oxygenated hemoglobin. A preferred reagent includes cyanide as the active ingredient.

4 Claims, No Drawings

ZINC PROTOPORPHYRIN TEST SYSTEM

BACKGROUND OF THE INVENTION

The present invention relates to the assay of zinc protoporphyrin in whole blood and, more particularly, to a reagent that permits the determination of zinc protoporphyrin levels by hematofluorometry without the required oxygenation or re-oxygenation of hemoglobin in intact erythrocytes.

It has been well established that the determination of zinc protoporphyrin is important in the diagnosis and treatment of various diseases and deficiencies. For example, the determination of zinc protoporphyrin in blood is important in detecting iron deficiency, which affects an estimated 20% of the world's population, and in screening lead poisoning, which remains an environmental and occupational hazard. Equally, the determination of zinc protoporphyrin is important and useful in monitoring therapy or treatment for either of the above noted conditions.

For more than 10 years, a common method to screen for chronic lead exposure or iron deficiency has been to measure the zinc protoporphyrin level of whole blood. This has been most often accomplished using an instrument, the hematofluorometer, which is designed for front-surface fluorometry of whole blood. In making measurements, however, if the hemoglobin is not fully oxygenated, the hematofluorometer gives falsely low values due to a spectral shift of the hemoglobin. To overcome this problem, it was necessary in the past to verify that the hemoglobin was fully oxygenated, and this was accomplished by stirring or aeration of the blood specimens followed by three or more successive readings with the fluorometer. If the several readings were substantially identical, this was an indication of fully oxygenated hemoglobin and thus a relatively accurate zinc protoporphyrin level.

As may be appreciated, there are inherent possibilities for error in the aforementioned system. In addition, this approach to oxygenation is time consuming and thus, less economical. Finally, stored or aged blood becomes much more difficult, if not impossible, to fully oxygenate by existing procedures.

SUMMARY OF THE INVENTION

Prior to the present invention, there was no approach to making one, accurate and dependable reading of zinc protoporphyrin fluorescence by hematofluorometry. The present invention overcomes this shortcoming by providing a new and improved approach to zinc protoporphyrin analysis by reacting the hemoglobin with a reagent to produce a stable coordination product which has a similar spectrum (in the desired optical range) to oxygenated hemoglobin. More particularly, the present invention produces a derivatized hemoglobin which has a similar spectrum as oxygenated hemoglobin, or oxyhemoglobin, the form of hemoglobin present when zinc protoporphyrin should actually be measured. To be effective for use in hematofluorometry, a derivatizing reaction must occur rapidly while preserving the erythrocyte intact.

The present invention provides this derivatized hemoglobin through the use of a cyanide-based reagent. The use of the cyanide-based reagent results in a cyanide-hemoglobin derivative having essentially the same spectral properties as hemoglobin.

DETAILED DESCRIPTION OF THE INVENTION

The present invention includes a reagent and a method of use of the reagent to form a derivatized hemoglobin having essentially the same spectral properties as oxyhemoglobin (within the spectral range under consideration utilizing an hematofluorometer). The preferred reagent includes a source of cyanide, such as about 0.2 mol/L potassium cyanide as the active ingredient to form a cyanide hemoglobin coordination complex. The reagent should also include beta-D-fructofuranosyl-alpha-D-glucopyranoside (i.e., sucrose) in the amount of about 0.3 mol/L as a stabilizer to provide better overall reaction conditions. One critical factor is the cyanide ion concentration in the reagent, as it is this factor which affects the overall efficiency of the system. A second critical factor is the pH, which optimizes the reaction condition for rapid, quantitative conversion of the hemoglobin.

Using the ingredients and amounts referred to above, a total volume of 5 L should be formulated. The concentration range of potassium cyanide should be 0.05–0.30 mol/l while the range of beta-D-fructofuranosyl-alpha-D-flucopyranoside should be 0.2–0.4 mol/L. All compounds should be ACS reagent grade. The pH of the system should be approximately $11\pm0.2$ to effect virtually instantaneous and complete reaction between cyanide and hemoglobin.

The manufacturing procedure is to first add beta-D-fructofuranosyl-alpha-D-glucopyranoside and stir until dissolved and then add the potassium cyanide and stir until dissolved.

It is within the spirit and scope of the present invention to provide the cyanide ions not only through the use of potassium cyanide but through other cyanide sources as well. Equally, it is within the spirit and scope of the present invention to utilize stabilizing agents other than beta-D-fructofuranosyl-alpha-D-glucopyranoside. Lastly, it is within the spirit and scope of the present invention to utilize other possible coordinating substances to derivatize the hemoglobin.

In the use of the reagent of the present invention, one or two drops of the reagent should be added to a typical, standard-sized sample (usually one or two drops) of whole blood heretofore used for fluorometric analysis.

The foregoing is a complete description of the present invention. Various changes may be made without departing from the spirit and scope thereof, and the invention should be limited only by the following claims.

What is claimed is:

1. In a method of analyzing a blood sample for zinc protoporphyrin levels by subjecting the sample to hematofluorometry within a predetermined spectral range, the improvement comprising:
    adding a reagent which includes cyanide ions to the blood sample to react with hemoglobin and produce a cyanide-hemoglobin coordination complex having essentially the same spectral properties as oxygenated hemoglobin in the predetermined spectral range and carrying out said method without fully oxygenating hemoglobin in the blood sample.

2. The method as defined in claim 1 wherein the reagent includes potassium cyanide as a source for the cyanide ions.

3. The method as defined in claim 1 wherein the reagent includes sucrose along with the cyanide ions to aid in reacting hemoglobin and cyanide ions.

4. The method as defined in claim 3 wherein the molar ratio of cyanide to sucrose in the reagent is approximately 2:3.

* * * * *